(12) United States Patent
Cedeno

(10) Patent No.: US 8,197,402 B1
(45) Date of Patent: Jun. 12, 2012

(54) FREE-HAND LARYNGOSCOPE GAPER

(76) Inventor: Douglas Alexis Cedeno, Distrito Capital (VE)

(*) Notice: Subject to any disclaimer, the term of this patent is extended or adjusted under 35 U.S.C. 154(b) by 307 days.

(21) Appl. No.: 12/486,145

(22) Filed: Jun. 17, 2009

(51) Int. Cl.
*A61B 1/267* (2006.01)
(52) U.S. Cl. ........................................ 600/194
(58) Field of Classification Search ........... 600/185–245
See application file for complete search history.

(56) References Cited

U.S. PATENT DOCUMENTS

| | | | |
|---|---|---|---|
| 1,601,035 A * | 9/1926 | Nauth | 600/217 |
| 3,913,568 A | 10/1975 | Carpenter | |
| 4,024,859 A * | 5/1977 | Slepyan et al. | 600/215 |
| 4,213,451 A * | 7/1980 | Swenson | 600/215 |
| 4,337,761 A | 7/1982 | Upsher | |
| 4,793,327 A * | 12/1988 | Frankel | 600/194 |
| 4,915,626 A | 4/1990 | Lemmey | |
| D332,140 S | 12/1992 | La Bombard et al. | |
| 5,174,283 A * | 12/1992 | Parker | 128/200.26 |
| 5,381,787 A * | 1/1995 | Bullard | 600/188 |
| 5,938,591 A * | 8/1999 | Minson | 600/191 |
| 5,964,217 A | 10/1999 | Christopher | |
| 6,090,040 A * | 7/2000 | Metro | 600/196 |
| 7,787,483 B2 * | 8/2010 | Vanderhaegen et al. | 370/426 |
| 2005/0192481 A1 | 9/2005 | Berci et al. | |
| 2008/0103364 A1 * | 5/2008 | Shapiro | 600/185 |

* cited by examiner

*Primary Examiner* — Eduardo C Robert
*Assistant Examiner* — James Palmer
(74) *Attorney, Agent, or Firm* — Kyle Fletcher

(57) ABSTRACT

The laryngoscope gaper is a hands free medical device that keeps the patient's mouth open for the introduction of a flexible or rigid endoscope or for the introduction of a tracheal tube. The device includes a mouthpiece with teeth locator, tongue retractor, and laryngoscope guides. The tongue retractor and the mouth piece work to maintain the mouth in an open position during use of the laryngoscope.

4 Claims, 5 Drawing Sheets

FREE-HAND LARYNGOSCOPE GAPER

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

A. Field of the Invention

The present invention relates to the field of medical devices used in the performance of tracheal intubation or for the introduction of an endoscope, more specifically, a medical device that combines a maxillo-lingual separator with an articulated top support.

B. Discussion of the Prior Art

As a preliminary note, it should be stated that there is an ample amount of prior art that deals with laryngoscopic tools. As will be discussed immediately below, no prior art discloses a laryngoscopic tool that is hands-free.

The Lemmey patent (U.S. Pat. No. 4,915,626) discloses a dental inspection apparatus to view an image of the interior of the mouth of a patient and contemporaneously display a video image of the interior of the mouth. However, the apparatus of the Lemmey patent does not have a means for guiding an endotracheal tube.

The Upsher patent (U.S. Pat. No. 4,337,761) discloses a laryngoscope having a curved blade provided with means on the blade for removably holding an endotracheal tube and for guiding such tube into the pharynx, larynx, and trachea. However, the laryngoscope of the Upsher patent does not have an articulated top support that impacts the bottom of the patient's nose, in order to provide a means with which to keep the patient's mouth open while provide guiding and/or supporting means for the introduction of the endotracheal tube.

The Carpenter patent (U.S. Pat. No. 3,913,568) discloses an instrument for examining the nasopharynx and larynx, which has optical fibers. However, the instrument of the Carpenter patent does not include a means within which to keep the patient's mouth open, nor does the instrument include a means within which to keep the glottis exposed in order to introduce a tracheal tube.

The Christopher patent (U.S. Pat. No. 5,964,217) discloses an endotracheal tube which can be inserted into a patient's trachea during resuscitation by using a face mask and a curved guide, which allows for hands-free operation. However, the endotracheal tube of the Christopher patent does not include an articulated top that impacts the bottom of the patient's nose as the means of keeping the patient's mouth open, nor does the tube keep the glottis exposed for introduction of a rigid or flexible endoscope for visual examination.

The Berci et al. Patent Application Publication (U.S. Pub. No. 2005/0192481) discloses a laryngoscope with a detachable camera. However, the laryngoscope of the Berci publication does not include an articulated top for impaction with the bottom of the patient's nose, nor does the device include a means with which to keep the patient's mouth open.

The Metro patent (U.S. Pat. No. 6,090,040) discloses an automatic positioning and retracting laryngoscope, detachable periscope, and method of endotracheal intubation that provides hands free operation and has optical fibers. However, the device of the Metro patent has a blade (30) that impacts the bottom surface of the top teeth of the patient's mouth in order to keep the patient's mouth open, as opposed to impacting the bottom surface of the patient's nose.

The La Bombard et al. patent (U.S. Pat. No. Des. 332,140) illustrates a design for a tracheostomy tube, which does not depict a means to keep the mouth of a patient open.

While the above-described devices fulfill their respective and particular objects and requirements, they do not describe a hands-free laryngoscope gaper that provides for the advantages of hands-free laryngoscope gaper.

BRIEF SUMMARY OF THE INVENTION

The laryngoscope gaper is a hands free medical device that keeps the patient's mouth open for the introduction of a flexible or rigid endoscope or for the introduction of a tracheal tube. The device includes a mouthpiece with teeth locator, tongue retractor, and laryngoscope guides. The tongue retractor and the mouth piece work to maintain the mouth in an open position during use of the laryngoscope.

An object of the invention is to provide a laryngoscope gaper that supports said laryngoscope in a hands-free manner wherein the mouth is opened when the device is in use.

A further object of the invention is to provide a gaper that supports the mouth in an open position via a tongue retractor and mouthpiece having teeth locator.

A further object of the invention is to provide a plurality of guides suited for support of a light and/or laryngoscope.

These together with additional objects, features and advantages of the hands-free laryngoscope gaper will be readily apparent to those of ordinary skill in the art upon reading the following detailed description of presently preferred, but nonetheless illustrative, embodiments of the hands-free laryngoscope gaper when taken in conjunction with the accompanying drawings.

In this respect, before explaining the current embodiments of the hands-free laryngoscope gaper in detail, it is to be understood that the hands-free laryngoscope gaper is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the hands-free laryngoscope gaper.

It is therefore important that the claims be regarded as including such equivalent construction insofar as they do not depart from the spirit and scope of the hands-free laryngoscope gaper. It is also to be understood that the phraseology and terminology employed herein are for purposes of description and should not be regarded as limiting.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE EMBODIMENT

Figure 1:
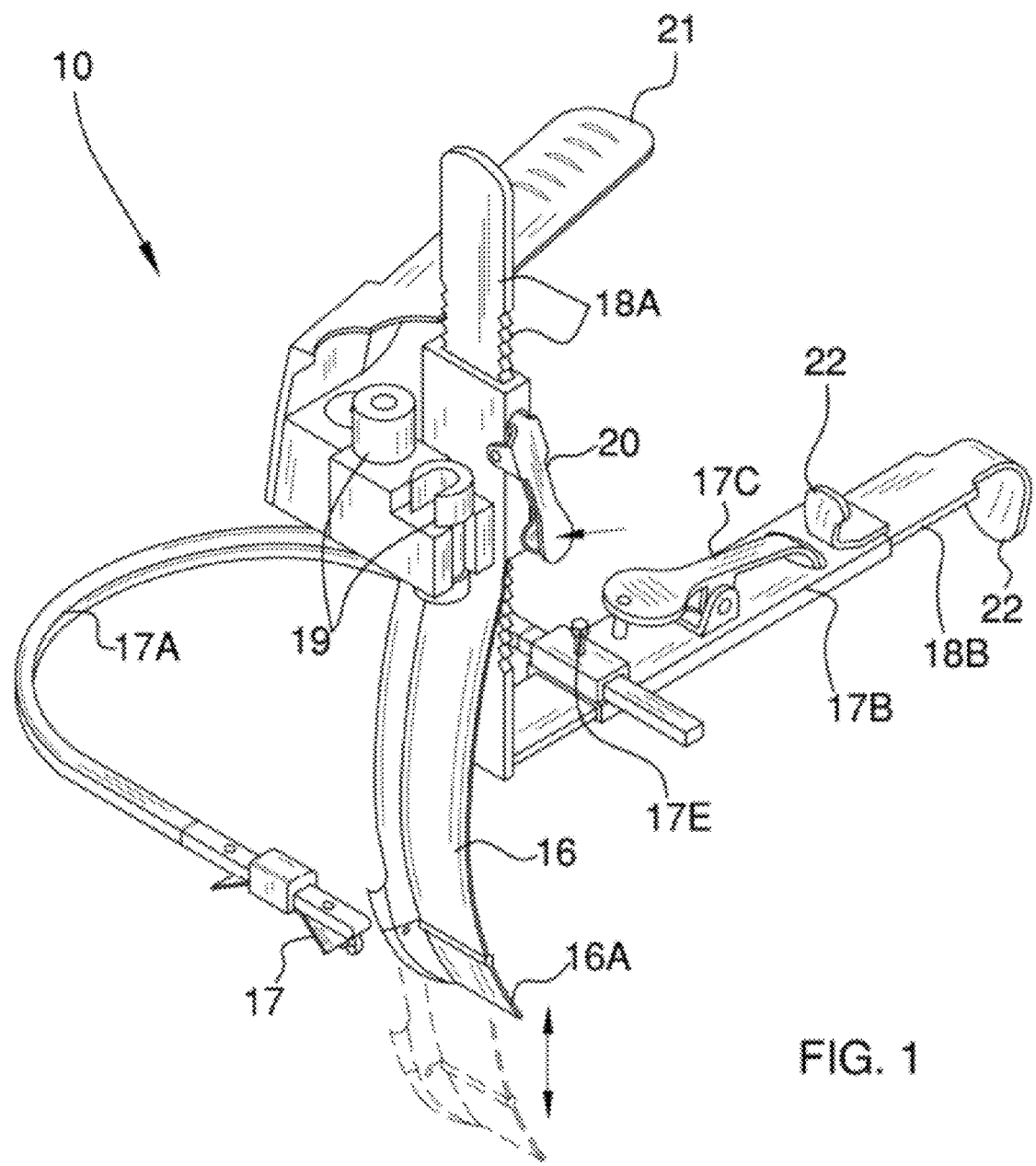
FIG. 1 illustrates an isometric view of the laryngoscope gaper with a vertical arrow indicating vertical movement of the tongue retractor.
Figure 2:
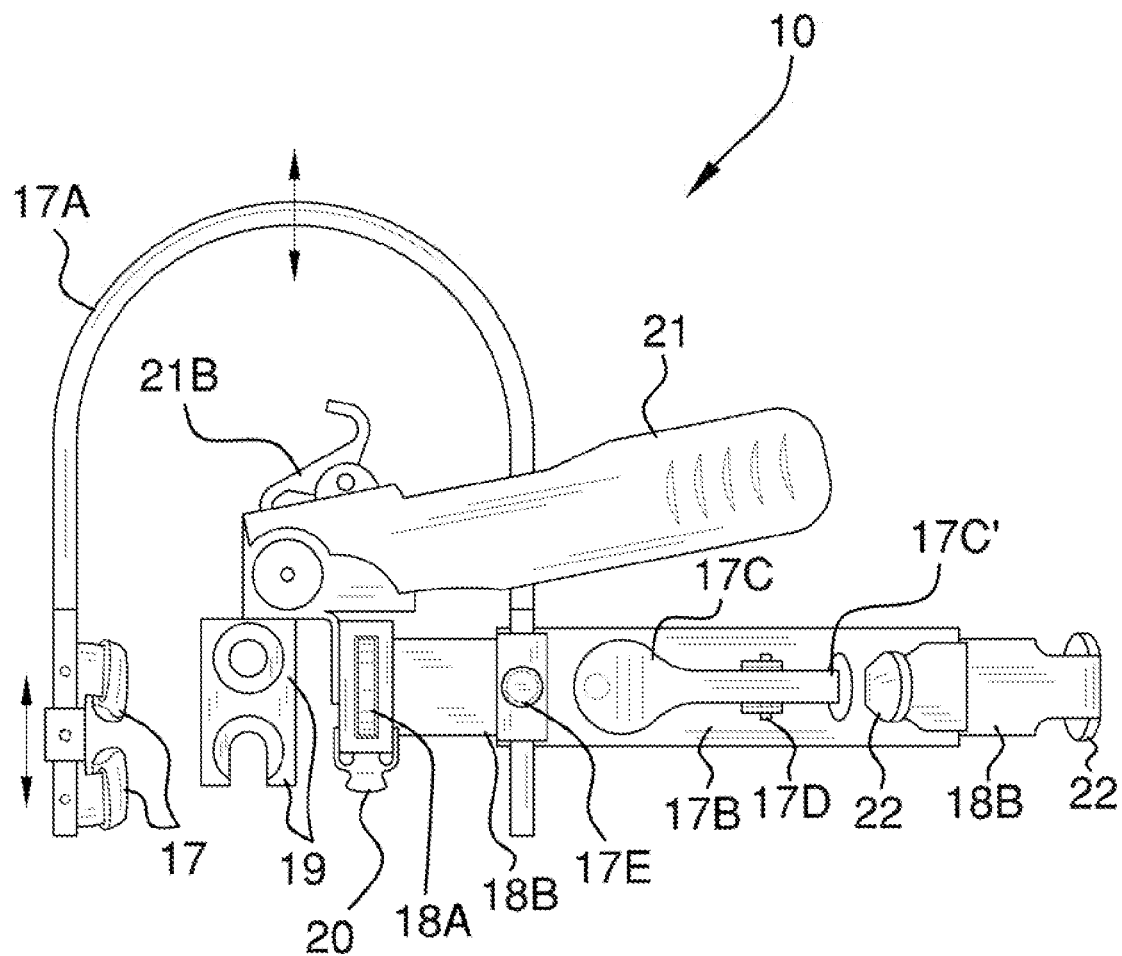
FIG. 2 illustrates a top view of the laryngoscope gaper with vertical arrows indicating vertical movement of the mouth piece and teeth locator with respect to the rest of said gaper.
Figure 3:
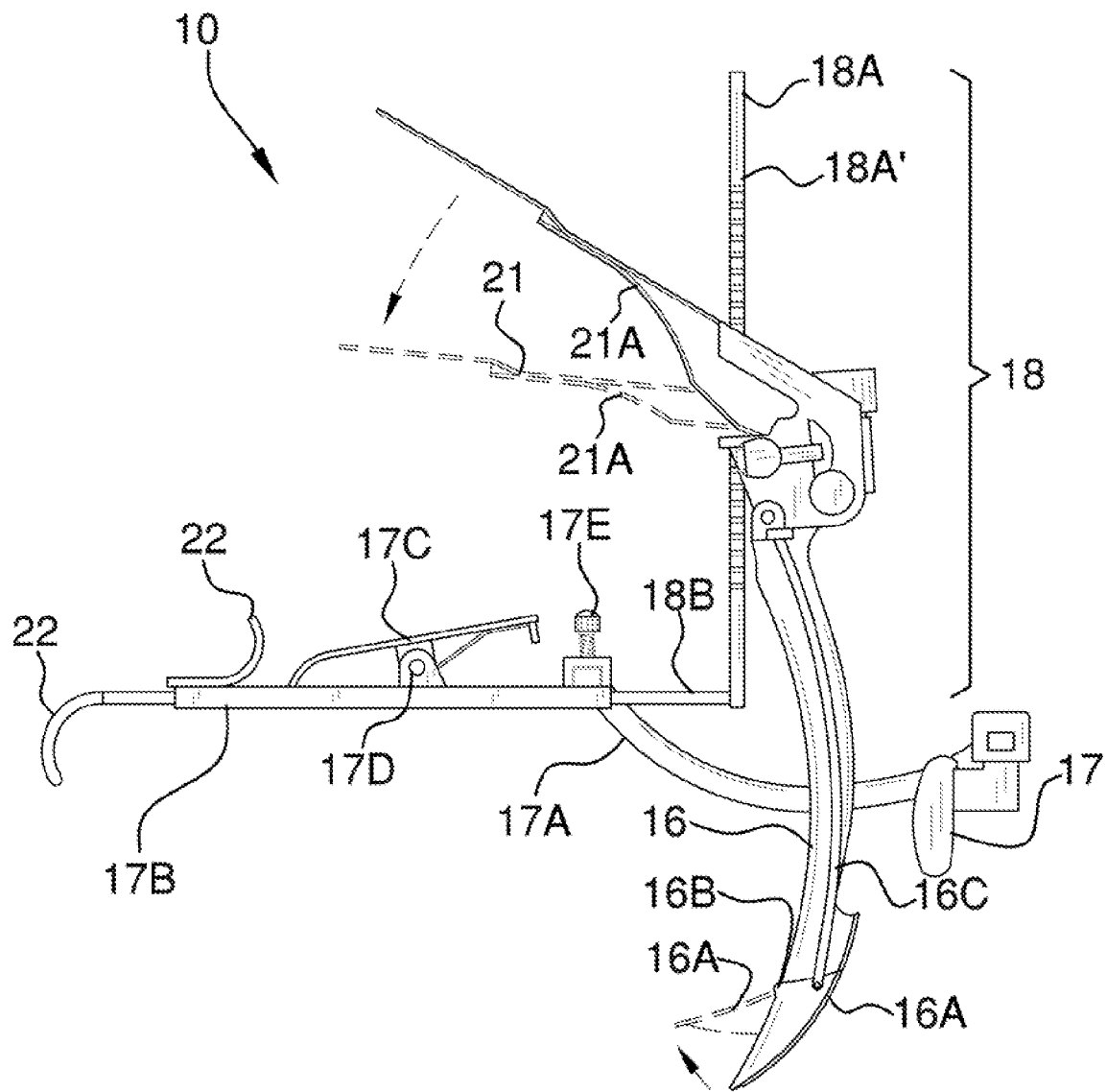
FIG. 3 illustrates a side view of the laryngoscope gaper with an arrow indicating rotational movement of the tongue retractor, and an arrow indicating rotational movement of the tongue retractor lever.
Figure 4:
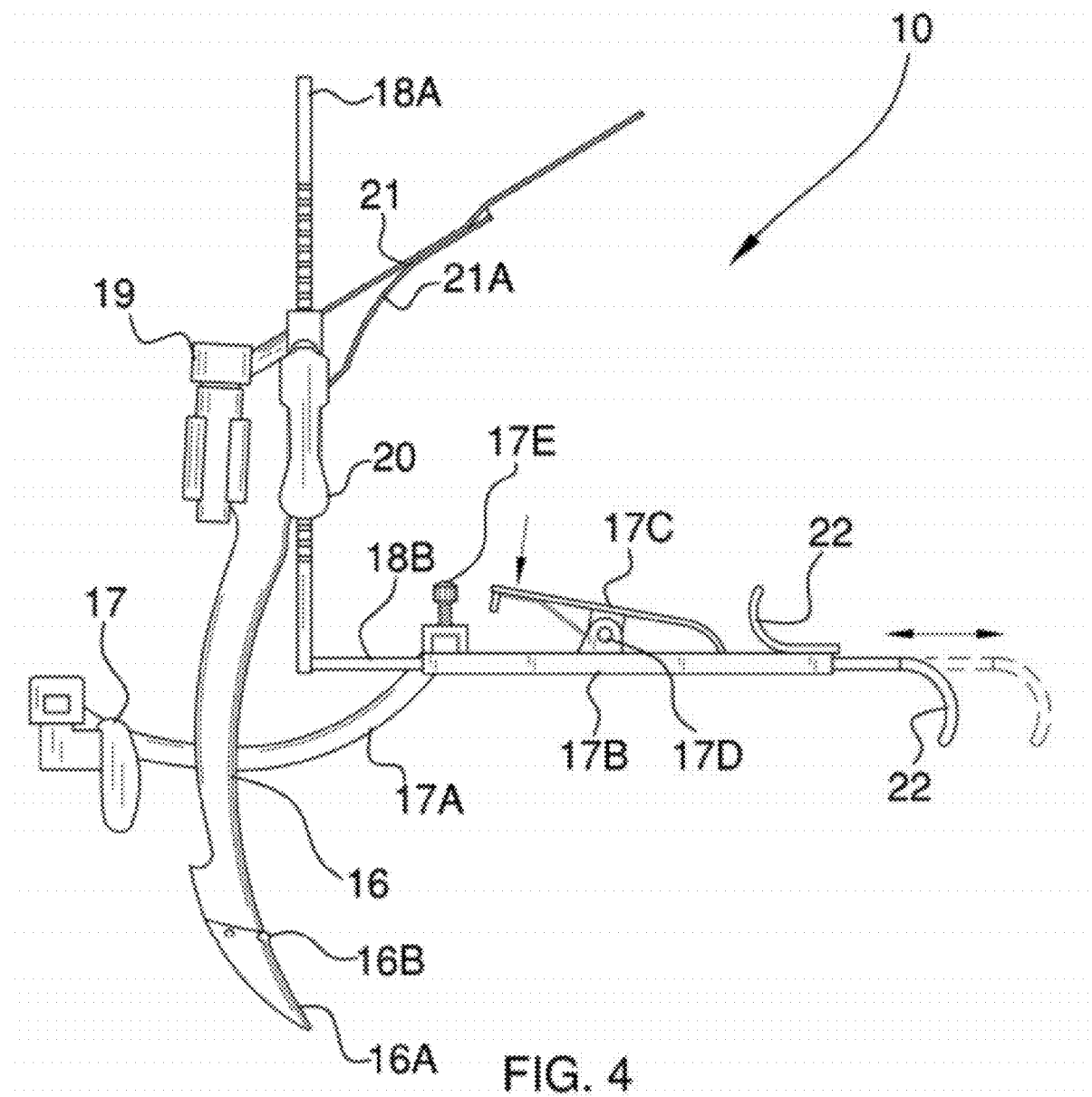
FIG. 4 illustrates a right side view of the laryngoscope gaper with a horizontal arrow indicating horizontal movement of the horizontal adjustment piece and a nearly vertical arrow indicating how the horizontal release tab moves.
Figure 5:
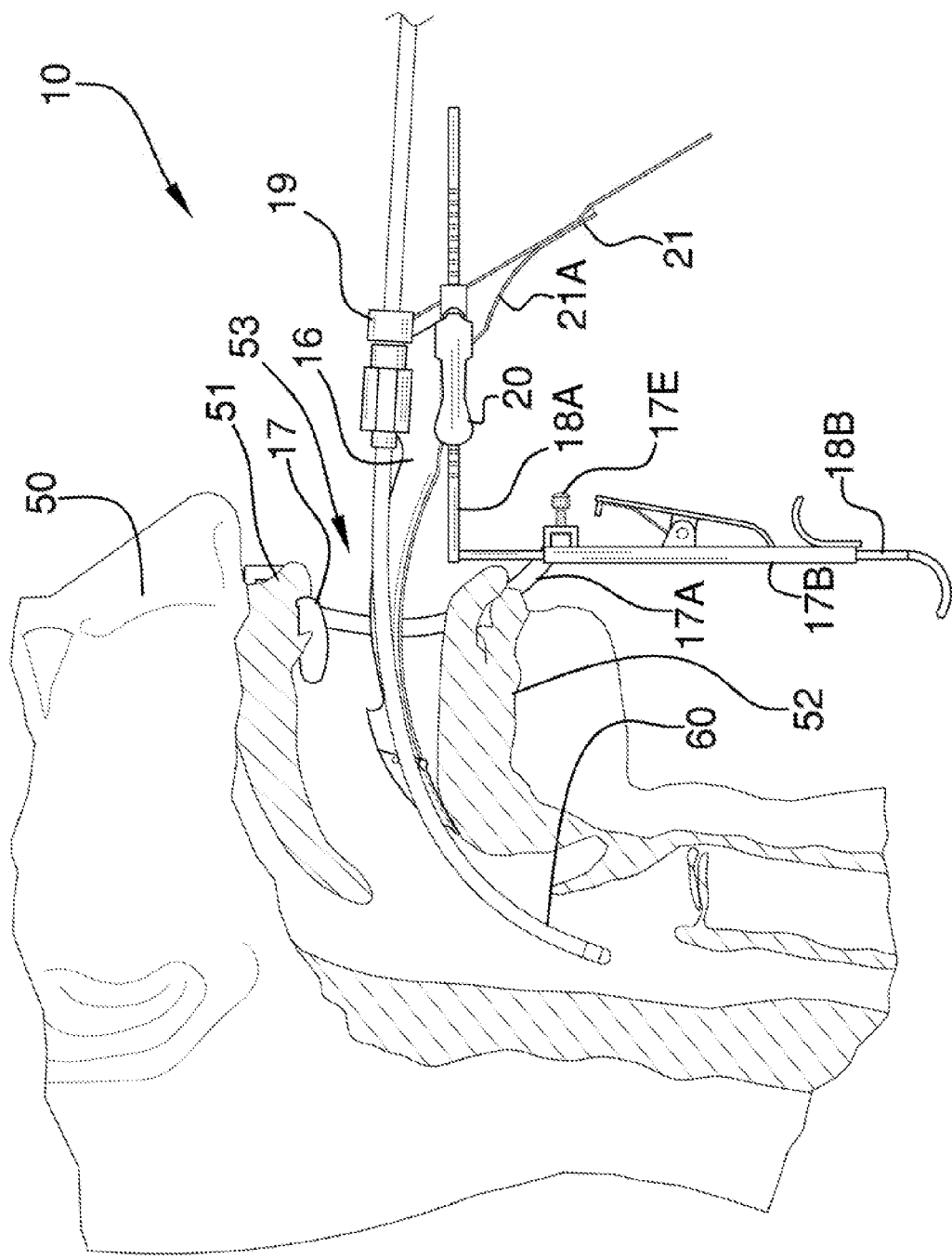
FIG. 5 illustrates a side view of the laryngoscope gaper in use with the tongue retractor suppressing a tongue and a laryngoscope being inserted into the throat of an individual via the laryngoscope gaper.

Detailed reference will now be made to the preferred embodiment of the present invention, examples of which are illustrated in FIGS. 1-5. A hands-free laryngoscope gaper 10 (hereinafter invention) that is used in performing a tracheal intubation, laryngoscopy, fibro-bronchoscopy, or any procedure involving a scope that passes down the trachea. The invention 10 includes a tongue retractor 16, a teeth locator 17, a base 18, and endoscope/light guides 19.

The teeth locator 17 is designed to impact a bottom surface of a patient's 50 upper teeth 51. The tongue retractor 16 touches a rear of a tongue 52 of the patient 50. The invention 10 works by keeping a mouth 53 of the patient 50 open while performing a medical procedure by impacting the bottom of the upper teeth 51 and the rear of the tongue 52 of the patient 50, via the tongue retractor 16 and the teeth locator 17.

The base 18 is composed of a vertical member 18A, and a horizontal member 18B. The horizontal member 18B extends perpendicularly from the vertical member 18A.

The vertical member 18A has a plurality of notches 18A' along the length of the vertical member 18A. A vertical release tab 20 connects to the tongue retractor 16, and provides vertical movement of the tongue retractor 16 along the vertical member 18A. The vertical release tab 20 has a locking mechanism (not depicted) that can secure the tongue retractor 16 in place, or move vertically. The locking mechanism (not depicted) traverses and locks upon the notches 18A' of the vertical member 18A.

The tongue retractor 16 has a retracting tip 16A that can move rotational via a hinge 16B. The retracting tip 16A is actuated via a tongue retractor lever 21 that is connected to the retracting tip 16A via a tip linkage 16C. The inclusion of the retracting tip 16A is to prevent the tongue 52 from retracting backwards down the throat by contouring the tongue retractor 16 and retracting tip 16A along the throat. The tongue retractor lever 21 has a spring-loaded action via a spring member 21A that imposes a biasing force upon the tongue retractor lever 21 when depressed (see FIG. 3), which locks into place when depressed down thereby moving the retracting tip 16A. To release this action, a tongue retractor release 21B is included that will unlock the tongue retractor lever 21 to its normal position via the spring member 21A.

The endoscope/light guides 19 attach to the tongue retractor 16, and provide support to and alignment of an endoscope 60.

The teeth locator 17 attaches to a mouthpiece 17A that in turn attaches to a horizontal adjustment piece 17B via a mouthpiece adjustment lock screw 17E. The mouthpiece adjustment piece 17B adjust the lateral distance of the teeth locator 17 with respect to the tongue retractor 16.

The horizontal adjustment piece 17B slides upon the horizontal member 18B, and adjusts the vertical length of the teeth locator 17 with respect to the base 18. The horizontal adjustment piece 17B can either slide or be locked in place with respect to the horizontal member 18B via a horizontal release tab 17C that rotates about a pivot point 17D, and of which is biased upon by a spring (not depicted). Wherein the horizontal release tab 17C has an arm 17C' that engages a notch (shown). The horizontal member 18B has the plurality of notches (not depicted) that interact with the arm 17C' of the horizontal release tab 17C in order to secure the horizontal release tab 17C with respect to the horizontal member 18B.

Movement of the horizontal adjustment piece 17B is accommodated by thumb pulls 22 located on both the horizontal adjustment member 17B and horizontal member 18. The thumb pulls 22 enable a medical practitioner the ability to extend or retract the horizontal adjustment member 17B relative the horizontal member 18B (see FIG. 4).

The inclusion of the horizontal adjustment piece 17B and the mouthpiece adjustment lock screw 17E is to enable lateral and vertical adjustments be made to the teeth locator 17 with respect to the tongue retractor 16 and base 18, respectively. The mouthpiece adjustment lock screw 17E simply locks onto or is released from the horizontal adjustment piece 17B by tightening or loosening said mouthpiece adjustment lock screw 17E.

The invention 10 is made of a material comprising a plastic or medical grade stainless steel.

With respect to the above description, it is to be realized that the optimum dimensional relationship for the various components of the invention 10, to include variations in size, materials, shape, form, function, and the manner of operation, assembly and use, are deemed readily apparent and obvious to one skilled in the art, and all equivalent relationships to those illustrated in the drawings and described in the specification are intended to be encompassed by the invention 10.

Variations and alternatives of the present embodiment including equivalent structures and structural equivalents are readily apparent to those of ordinary skill in the art upon reading the present disclosure, and such variations and alternatives are incorporated in the invention unless otherwise expressly indicated in the claims.

The inventor claims:

1. A hands free laryngoscope gaper further comprising:
   wherein said gaper has a base from which a tongue retractor and teeth locator extend in order to keep a mouth of a patient open for intubation by having a length sufficient to extend said mouth open; at least one guide is provided along said tongue retractor in order to support and align an endoscope or light;
   wherein said tongue retractor suppresses movement of a tongue and includes a retracting tip pivotally hinged along a bottom end of said tongue retractor, wherein said retracting tip is actuated via a link and retractor lever; and
   wherein said teeth locator is configured to impact a top row of teeth;
   wherein the retractor lever has a spring member to lock said retractor lever, which locks said retracting tip in a lowered position;
   wherein the retractor lever is unlocked from said spring member via a tongue retractor release;

wherein said tongue retractor moves vertically along said base via a vertical member;

wherein said teeth locator attaches to said base via a mouthpiece;

wherein said vertical member can lock in place upon said base via a locking means;

wherein said locking means can be unlocked in order to enable movement of both the vertical member and tongue retractor with respect to the base;

wherein said mouthpiece extends from said base and bends around said tongue retractor;

wherein said teeth locator moves laterally from said base via a mouthpiece adjustment lock screw;

wherein said teeth locator moves horizontally from said base via a horizontal adjustment piece, which attaches to the mouthpiece and is slideably engaged with said base; and wherein said teeth locator moves horizontally in order to adjust the size of the opening of the mouth by adjusting the length of the distance between said base and said teeth locator;

wherein said base and said horizontal adjustment piece have thumb pulls that enable movement back and forth of the horizontal adjustment piece with respect to said base via a single hand.

2. The laryngoscope gaper as described in claim 1 wherein said base, teeth locator, tongue retractor are made of a material comprising a metal or plastic.

3. A hands free laryngoscope gaper further comprising:

wherein said gaper has a base from which a tongue retractor and teeth locator extend in order to keep a mouth of a patient open for intubation by having a length sufficient to extend said mouth open; at least one guide is provided along said tongue retractor in order to support and align an endoscope or light;

wherein said tongue retractor suppresses movement of a tongue and includes a retracting tip pivotally hinged along a bottom end of said tongue retractor, wherein said retracting tip is actuated via a link and retractor lever; and wherein said teeth locator is configured to impact a top row of teeth;

wherein the retractor lever has a spring member to lock said retractor lever, which locks said retracting tip in a lowered position;

wherein the retractor lever is unlocked from said spring member via a tongue retractor release;

wherein said tongue retractor moves vertically along said base via a vertical member;

wherein said vertical member can lock in place upon said base via a locking means;

wherein said locking means can be unlocked in order to enable movement of both the vertical member and tongue retractor with respect to the base;

wherein said teeth locator attaches to said base via a mouthpiece;

wherein said mouthpiece extends from said base and bends around said tongue retractor;

wherein said teeth locator moves laterally from said base via a mouthpiece adjustment lock screw;

wherein said teeth locator moves horizontally from said base via a horizontal adjustment piece, which attaches to the mouthpiece and is slideably engaged with said base; and wherein said teeth locator moves horizontally in order to adjust the size of the opening of the mouth by adjusting the length of the distance between said base and said teeth locator;

wherein said base and said horizontal adjustment piece have thumb pulls that enable movement back and forth of the horizontal adjustment piece with respect to said base via a single hand.

4. The laryngoscope gaper as described in claim 3 wherein said base, teeth locator, tongue retractor are made of a material comprising a metal or plastic.

* * * * *